(12) United States Patent
Fu et al.

(10) Patent No.: US 7,713,205 B2
(45) Date of Patent: May 11, 2010

(54) DYNAMIC TRACKING OF SOFT TISSUE TARGETS WITH ULTRASOUND IMAGES, WITHOUT USING FIDUCIAL MARKERS

(75) Inventors: Dongshan Fu, Santa Clara, CA (US); Gopinath Kuduvalli, San Jose, CA (US); John Allison, Los Altos, CA (US)

(73) Assignee: Accuray Incorporated, Sunnyvale, CA (US)

( * ) Notice: Subject to any disclaimer, the term of this patent is extended or adjusted under 35 U.S.C. 154(b) by 1079 days.

(21) Appl. No.: 11/172,097

(22) Filed: Jun. 29, 2005

(65) Prior Publication Data

US 2007/0015991 A1    Jan. 18, 2007

(51) Int. Cl.
*A61B 8/00*    (2006.01)
(52) U.S. Cl. ........................ 600/443; 600/437
(58) Field of Classification Search .............. 600/437, 600/443, 411, 439, 413, 425, 427, 428; 378/62, 378/63, 65
See application file for complete search history.

(56) References Cited

U.S. PATENT DOCUMENTS

| | | | | |
|---|---|---|---|---|
| 6,139,499 | A * | 10/2000 | Wilk | ........................ 600/443 |
| 6,144,875 | A | 11/2000 | Schweikard et al. | |
| 6,277,074 | B1 * | 8/2001 | Chaturvedi et al. | ......... 600/437 |
| 6,307,914 | B1 | 10/2001 | Kunieda et al. | |
| 6,390,982 | B1 * | 5/2002 | Bova et al. | ................. 600/443 |
| 6,501,981 | B1 * | 12/2002 | Schweikard et al. | ........ 600/427 |
| 6,778,850 | B1 | 8/2004 | Adler et al. | |
| 2002/0138004 | A1 * | 9/2002 | Dickey et al. | ................ 600/443 |
| 2003/0125622 | A1 | 7/2003 | Schweikard et al. | |
| 2003/0220561 | A1 * | 11/2003 | Camus et al. | ................ 600/424 |
| 2005/0027194 | A1 | 2/2005 | Adler et al. | |
| 2005/0059887 | A1 * | 3/2005 | Mostafavi et al. | ........... 600/427 |
| 2005/0090742 | A1 * | 4/2005 | Mine et al. | ................... 600/443 |
| 2006/0293598 | A1 * | 12/2006 | Fraser | ........................ 600/439 |

OTHER PUBLICATIONS

J.B. Antoine Maintz, Max A. Viergever, "A Survey of Medical Image Registration", Medical Image Arrays (1998) vol. 2, No. 1, pp. 1-37.
A. Schweikard, H. Shiomi, J. Adler, "Respiration tracking in radiosurgery without fiducials", Int. J. Medical Robotics and Computer Assisted Surgery, 2005, 1(2): pp. 19-27.

(Continued)

*Primary Examiner*—Long V Le
*Assistant Examiner*—Saurel J Selkin
(74) *Attorney, Agent, or Firm*—Blakely, Sokoloff, Taylor & Zafman LLP

(57) ABSTRACT

An apparatus and method of dynamically tracking a soft tissue target with ultrasound images, without the use of fiducial markers. In one embodiment, the apparatus includes an ultrasound imager to generate a reference ultrasound and a first ultrasound image having a soft tissue target, and a processing device coupled to the ultrasound imager to receive the reference ultrasound image and the first ultrasound image, to register the first ultrasound image with the reference ultrasound image, and to determine a displacement of the soft tissue target based on registration of the first ultrasound image with the reference ultrasound image.

5 Claims, 9 Drawing Sheets

OTHER PUBLICATIONS

Int'l PCT Search Report PCT/US06/25793, Mailing date: Sep. 26, 2007 (4 pages).

PCT Written Opinion PCT/US06/25793, Mailing date: Sep. 26, 2007 (10 pages).

Coste-Manière, È., "Robotic whole body stereotactic radiosurgery: clinical advantages of the CyberKnife® integrated system", The International Journal of Medical Robotics +Computer Assisted Surgery, 2005, www.roboticpublications.com, pp. 28-39.

PCT International Preliminary Report on Patentability, PCT/US2006/025793, International filing date Jun. 29, 2006, mailed Jan. 17, 2008.

* cited by examiner

DYNAMIC TRACKING OF SOFT TISSUE TARGETS WITH ULTRASOUND IMAGES, WITHOUT USING FIDUCIAL MARKERS

TECHNICAL FIELD

Embodiments of the present invention pertain to the field of radiation treatment and, in particular, to tracking of targets with ultrasound images during radiation treatment.

BACKGROUND

A tumor is an abnormal growth of tissue resulting from the uncontrolled, progressive multiplication of cells, serving no physiological function. A tumor may be malignant (cancerous) or benign. A malignant tumor is one that spreads cancerous cells to other parts of the body (metastasizes) through blood vessels or the lymphatic system. A benign tumor does not metastasize, but can still be life-threatening if it impinges on critical body structures such as nerves, blood vessels and organs (especially the brain).

A non-invasive method for tumor treatment is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source is changed, every beam passes through the tumor site, but passes through a different area of healthy tissue on its way to the tumor. As a result, the cumulative radiation dose at the tumor is high and the average radiation dose to healthy tissue is low. The term radiotherapy refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centi-Gray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted by the magnitude of the radiation One problem encountered in external beam radiation treatment is that pathological anatomies (e.g., a tumor) may move during treatment, which decreases accurate target localization (i.e., accurate tracking of the position of the target). Most notably, soft tissue targets tend to move with patient breathing during radiation treatment delivery sessions. Respiratory motion can move a tumor in the chest or abdomen, for example, by more than 3 centimeters (cm). In the presence of such respiratory motion, for example, it is difficult to achieve the goal of precisely and accurately delivering the radiation dose to the target, while avoiding surrounding healthy tissue. In external beam radiation treatment, accurate delivery of the radiation beams to the pathological anatomy being treated can be critical, in order to achieve the radiation dose distribution that was computed during the treatment planning stage.

One conventional solution for addressing the problem of tumor motion due to respiration is the use of gating techniques. Gating techniques dose not directly compensate for breathing motion, in that the radiation beam is not moved while it is being directed in the patient. Rather, the radiation beam is turned off when the tumor is thought to have moved from its reference position. However, a disadvantage of using a gating technique is that it significantly increases the amount to time required for delivering the radiation treatment. Another disadvantage is such an approach may result in inaccurate treatment of the tumor due to the assumptions made in tumor position.

One conventional solution for tracking motion of a target utilizes external markers (e.g., infrared emitters) placed on the outside of a patient (e.g., on the skin). The external markers are tracked automatically using an optical (e.g., infrared) tracking system. However, external markers cannot adequately reflect internal displacements caused by breathing motion. Large external patient motion may occur together with very small internal motion. For example, the internal target may move much slower than the skin surface.

Another conventional solution for tracking motion of a target involves the use of implanted fiducials. Typically, radiopaque fiducial markers (e.g., gold seeds or stainless steel screws) are implanted in close proximity to, or within, a target organ prior to treatment and used as reference points during treatment delivery. Stereo x-ray imaging is used during treatment to compute the precise spatial location of these fiducial markers (e.g., once every 10 seconds). However, internal markers alone may not be sufficient for accurate tracking. Yet another conventional solution combines the tracking of internal fiducial markers with the tracking of external markers in which x-ray imaging of the internal fiducial markers is synchronized with the optical tracking of the external markers. However, such a combined tracking approach still has the disadvantage of requiring the tracking of internal fiducial markers.

The tracking of internal fiducial markers can be difficult for the patient, because high accuracy tends to be achieved by using bone-implanted fiducial markers. The implanting of fiducial markers in bone requires a difficult and painful invasive procedure, especially for the C-spine, which may frequently lead to clinical complications. In addition, tracking bone-implanted fiducial markers may still may not provide accurate results for movement or deformation of soft tissue targets. Moreover, whether the fiducial marker is implanted in the bone or injected through a biopsy needle into soft tissue in the vicinity of the target area under computerized tomography (CT) monitoring, the patient must still undergo such invasive procedures before radiation treatment.

A conventional technique that tracks the motion of a tumor without the use of implanted fiducial markers is described in A. Schweikard, H Shiomi, J. Adler, Respiration Tracking in Radiosurgery Without Fiducials, Int J Medical Robotics and Computer Assisted Surgery, January 2005, 19-27. The described fiducial-less tracking technique use deformation algorithms on CT data sets, combined with registration of digitally reconstructed radiographs (DRR) and intra-treatment X-ray images of nearby bony landmarks (where the tumor itself may not be visible in the x-ray image in most cases) to obtain intermittent information on the tumor location. This target location information is then combined with conventional correlation techniques to achieve real-time tracking.

One disadvantage with all the above described conventional methods is that, with the exception of external marker tracking, they require the repeated exposure of the patient to non-therapeutic radiation from the intra-treatment x-rays that are taken to obtain intermittent information on the fiducial or target location.

BRIEF DESCRIPTION OF THE DRAWINGS

Embodiments of the present invention are illustrated by way of example, and not by way of limitation, in the figures of the accompanying drawings and in which.

DETAILED DESCRIPTION

Figure 1:
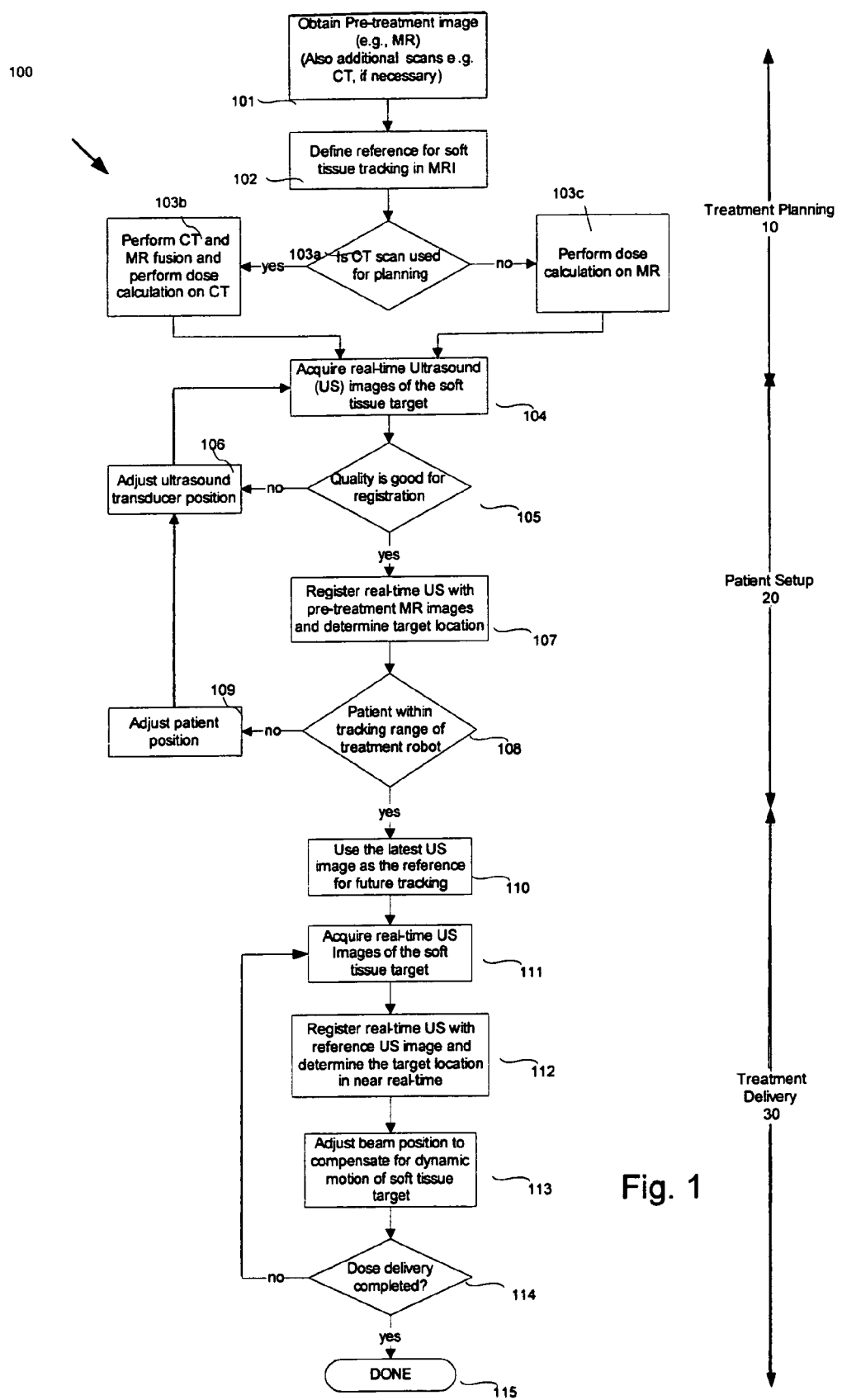
FIG. 1 is a flow chart illustrating one embodiment of a workflow for patient radiation treatment that includes near real-time tracking of a soft tissue target by registration of real-time US with the reference MR images (the reference US).

In the following description, numerous specific details are set forth such as examples of specific components, devices, methods, etc., in order to provide a thorough understanding of the present embodiments. It will be apparent, however, to one skilled in the art that these specific details need not be employed to practice the present embodiments. In other instances, well-known materials or methods have not been described in detail in order to avoid unnecessarily obscuring the present embodiments.

The term "coupled to" as used herein may mean coupled directly to or indirectly to through one or more intervening components. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines, and each of the single signal lines may alternatively be buses. The terms "first," "second," "third," "fourth," etc. as used herein are meant as labels to distinguish among different elements and may not necessarily have an ordinal meaning according to their numerical designation.

The term "real-time" in ultrasound imaging refers to synchronous acquisition and display of images without perceptible latency or flicker, for example, at a rate approximately greater than 1 Hertz (Hz). The term "near real-time" refers to a time scale that is slower than real-time, for example, by about one or more orders of magnitude less than the time scale of real-time. As an example, the time scale for acquiring x-ray images, which may range from about a fraction of a second to about several seconds may be considered near real-time.

Unless specifically stated otherwise as apparent from the following discussion, it is appreciated that throughout the description, discussions utilizing terms such as "processing" or "computing" or "calculating" or "determining" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices. Embodiments of the method described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the invention as described herein.

A dynamic tracking method and system is described for tracking movement of soft tissue targets without implanting fiducial markers in a patient that may be used, for example, with external beam radiation treatment. The method includes registration of one or more ultrasound (US) images, acquired during treatment delivery, to a pre-treatment image (e.g., MRI, CT, or fused MRI/CT), acquired as an initial reference image during treatment planning to determine and correct for initial patient movement during patient setup. The method may also include using one of the US images acquired during treatment delivery (e.g., most recently taken during treatment delivery) as a delivery stage reference image and performing real or near real-time registration of one or more subsequently acquired US images to the delivery stage reference image to determine and correct for patient motion during patient treatment delivery. The method may be employed using 2-D or 3-D ultrasound imaging techniques. Embodiments of the method described herein may enable fast, soft tissue tracking with real-time ultrasound imaging followed by near real-time registration of the US images with the reference US image.

In another embodiment, a dynamic tracking method and system are described for real-time soft tissue tracking, wherein real-time US image acquisition and US-US registration, is combined with real-time monitoring of one or more external markers disposed on a patient (e.g., LED's). The dynamic tracking method may also include building a mathematical model (e.g., correlation model) to relate the monitored-motion of the external markers to the location of the soft tissue obtained from registration of the real-time ultrasound images with the treatment delivery reference US image.

FIG. 1 illustrates one embodiment of a workflow for patient radiation therapy. It should be noted that one or more of the stages and/or step within a stage described in relation to FIGS. 1 and 2 may not necessarily be required for embodiments of the present invention, but are described in order to provide a better context for the discussion of certain embodiments of the present invention. Moreover, one or more steps illustrated and discussed as being within a particular stage, may be performed outside of that stage. It should also be noted that although embodiments describe herein refer to use with radiation treatment, the embodiments described herein may also be used in other applications that require dynamic tracking of soft tissue targets. The workflow 100 of FIG. 1 may also be discussed at times in reference to the treatment planning system 410 and treatment delivery system 420 of FIG. 4.

In the workflow 100 illustrated in FIG. 1, the patient radiation therapy includes a treatment planning stage 10, a patient setup stage 20, and a treatment delivery stage 30. The treatment planning stage 10 may include obtaining a pre-treatment image, using a first imaging modality, for example, magnetic resonance (MR) imaging, of a volume of interest (VOI) in the patient that includes a soft tissue target, step 101. Alternatively, the pre-treatment image may be acquired using other types of imaging modalities, for example, computerized tomography (CT), positron emission tomography (PET), fluoroscopy, etc. The treatment planning stage 10 may also include defining one or more reference points in the pre-treatment image with respect to which the location of the soft tissue target will be tracked during the dynamic tracking process (as discussed in further detail below) for treatment delivery, step 102. The reference tracking point may be one or more imageable landmarks in both ultrasound and the first modality. In MRI, CT and US images, the one or more imageable landmarks may be contours, shapes or edges of organs, or image content of tumors.

In this stage 10, other images (e.g., CT) may also be obtained that may be used in performing treatment planning, step 103a. Where, for example, a CT image has been obtained in step 103a, the CT image may be fused with the pre-treatment (e.g., MR) image to further facilitate dose calculation during inverse planning, step 103b. Alternatively, dose planning calculations may be performed using just the pre-treatment (e.g., MR) image obtained in step 101. It should be noted that steps 103a-c described for the treatment planning stage 10 are necessarily not required for practice of the embodiments of the present invention described below. It should be noted that although the workflow is discussed at times herein in regards to inverse planning, the methods herein may also be used with forward planning or a mixed planning in which part of the treatment dose is generated by isocenters placed using forward planning and part generated by individual beams during inverse planning.

The next stage of the workflow is the patient setup stage 20. At a time of patient setup, ultrasound images of the soft tissue area may be obtained, step 104. In one embodiment, a quality metric measure may be defined that will measure the quality of the registration. For the quality metric of US images, a visual determination may be used. When the US transducer is adjusted in such a way that the US image is visually similar to the reference image (MR or CT) in terms of image features such as organ contours and edges, the US image quality is acceptable for registration. The quality metric of the ultrasound images may be based upon multiple image parameters, for example, the technique of maneuvering the transducer (e.g., imaging sensor), the nature of the soft tissue and the surrounding area, the position and orientation of the imaging sensor, the amount of pressure applied using the imaging sensor, transmit frequency, receive frequency, gain, depth dependent gain, and dynamic range. The quality metric of the ultrasound image may also depend upon whether there is bone or air intervening between the tissue being imaged and the ultrasound imager. Alternatively, other imaging parameters known to those of ordinary skill in the art may be used in determining the quality metric of the image for registration purposes. The quality metric of the US image and the quality threshold may be used as a feedback to the ultrasound imaging system to adjust the imaging parameters to achieve the desired quality of the ultrasound images. In one embodiment, the ultrasound imager.(e.g., 620 of FIG. 6) may be repositioned to achieve the best quality of images. Thus, the patient setup stage 20 may include determining if the quality metric of the US image obtained meets a quality threshold for registration, step 105. If the quality metric of the US image does not meet the quality threshold, the ultrasound imager 620 may be adjusted or repositioned, step 106, with a return to step 104 for obtaining a better quality US image.

In step 107, the US image is registered with the pre-treatment image (e.g., MR) in order to determine the location or displacement of the soft tissue target with respect to the one or more reference points determined in step 102. Registration may be preformed using techniques known to those of ordinary skill in the art, for example, as described in "A Survey of Medical Image Registration" by Maintz and Viergeverm, Oxford University Press, 1998. Accordingly, a detailed description of registration is not provided. The accuracy and the success of registration may depend on the quality metric of the ultrasound images obtained in step 104. It should be noted that the one or more redundant ultrasound imagers may also be used to improve the chances of registering the output from at least one of the ultrasound imagers with the pre-treatment image. The redundant ultrasound imagers may be redundant ultrasound imaging arrays in the same transducer or, alternatively, in a separate transducer coupled to the body.

In one embodiment, to aid in the visualization of soft tissue structures and tumor boundaries, US contrast agents may be used to enhance the visualization of hyper- or hypo-vascular tumors. US contrast agents may be administered into the blood stream of the patient to circulate throughout the vascular system. US contrast agents increase the reflectivity of ultrasound, thereby enhancing the signal-to-noise ratio of echoes from contrast agent bubbles relative to surrounding tissues. In another embodiment, further improvement in visualization may be achieved by using US contrast agents with unique molecular binding properties that target a specific molecule associated with the target tumor. Such contrast agents will bind to target molecules in the tumor increasing their concentration and enabling better visualization with US. These contrast agents could also incorporate x-ray contrast properties to improve tumor visualization with x-rays.

In one embodiment, in step 108, the displacement of the soft tissue target determined by the registration (step 107) may be used to adjust the patient position such that the displacement is minimized to within an operating range of the treatment delivery system 420. This enables the radiation beam source to be controlled to deliver radiation beams as specified by the treatment plan. In one embodiment, if the patient is not within the operational range of the treatment delivery system, the method may include adjusting the position of the patient, step 109. It should be noted that if the patient is adjusted, the workflow may return to step 106, if desired, to adjust the ultrasound imager's position.

Alternatively, the patient step stage 20 may use other means for positioning the patient with the operational range of the treatment delivery system 420, for example, using X-ray/DRR registration in combination with CT data sets acquired during the treatment planning stage 10. The details of these conventional methods are known to those of ordinary skill in the art and, accordingly, are not included herein.

Once the initial patient setup 20 is completed, the workflow moves to the treatment delivery stage 30. In the treatment delivery stage 30, the latest ultrasound image may be recorded and used as a delivery reference US image for later US to US registration during treatment delivery, step 110. If the patient is well aligned during patient setup stage 20, a smaller volume of interest of the target VOI defined in the pre-treatment image may be used in the US images to achieve a faster registration. Alternatively, the same target region of interest defined in the pre-treatment image may be used. In one embodiment, the workflow progresses into an automatic tracking mode.

In automatic tracking mode, US images may be continuously acquired, step 111, at a real-time or near real-time imaging rate in that the images are acquired during the course of the treatment delivery stage 30 (i.e., while the treatment plan is being administered to the patient in a particular session). In one embodiment, for example, the US imaging rate may be approximately less than 60 Hz. Next, in step 112, one or more of the acquired US images (e.g., the latest or more recently acquired US image) may be registered with either the delivery reference US image (of step 110) or the pre-treatment image obtained in treatment planning (of step 101). In this embodiment, the dynamic motion of the soft tissue target with respect to the reference point of the reference image or reference US image may be computed as a function of time. Since the ultrasound imaging is performed in real-time, with sufficient computing power, the registration between the subsequently acquired US images in the session and the delivery reference US image may also be computed in near real-time.

As previously mentioned one or more redundant ultrasound imagers may also be used. In one embodiment, the registration results may be chosen from the ultrasound imager with the best quality metric. Alternatively, other known methods of deciding which ultrasound image to use may be implemented, for example, using a majority voting method.

In one embodiment, if the dose delivery according to the treatment plan is not completed, step 114, the workflow may return to step 111 where additional US images may be acquired.

In an alternative embodiment, once the initial patient set up is completed, the workflow may include the use of an external dynamic tracking system to enable faster tracking of the soft tissue targets than may be possible if only performing tracking based on the registration between the real-time US images and the delivery reference US image discussed above, as illustrated in FIG. 2. The results from the external dynamic tracking system are combined with the US registration results using a correlation model as discussed below.

In this embodiment, once the initial patient set up stage 20 is completed, the latest ultrasound image may be recorded and used as the delivery reference US image for later US to US registration during patient treatment, step 210. In automatic tracking mode of workflow 200 of FIG. 2, the ultrasound imager may be imaging at the imaging rate, described with respect to step 111 of FIG. 1, however, the ultrasound images obtained from the ultrasound imaging system may be sub-sampled in time at a rate (e.g., sampling rate) commensurate with the computing power available to perform the US to US registration, step 211. The sampled US image may be registered with either the latest reference US image or the pre-treatment image obtained in treatment planning, step 212.

The dynamic tracking system 402 may include one or more external markers (e.g., visible red or infrared LEDs) coupled to the patient and a tracker mounted in a treatment room to track the position of the one or more external markers. These external markers may be disposed on the exterior of the patient, for example, on the patient's skin or on a vest worn by the patient. In step 213, the dynamic tracker system acquires the position of the external markers in an arbitrary, but fixed, coordinate frame. The positions of the external markers are obtained at a scanning rate greater than the rate of the US imager. In one embodiment, the positions of the external markers are obtained in real-time. In one embodiment, for example, the scanning rate may be approximately greater than 1 Hz. Alternatively, other scanning rates may be used.

In order to combine the results from the external dynamic tracking system 402 with the US registration results, a correlation model is built, step 214. The motion of the external markers is determined in the fixed coordinate system that may be arbitrary with respect to the coordinate system for the US images and provided as input to a correlation engine (implemented by processing device 401). The correlation engine also receives the results of the registration of US images from step 212 as input. The results from the ultrasound image registration and that of the dynamic tracker are correlated by a mathematical model (e.g., correlation model), to give a mathematical relationship between the motion of the external markers measured in real-time, and that of the soft tissue target measured at the sampling rate by the ultrasound imaging system 620. In one embodiment, two US images may be registered to compute the correlation model with the corresponding motion of the one or more external markers. Accordingly, workflow 200 may further include, ultrasound imaging the soft tissue target at the imaging rate to obtain an additional US image, step 214*a*. The additional acquired US image may be registered with either the delivery reference US image or the pre-treatment image obtained in treatment planning, step 214*b*. The correlation model may then be updated, step 214*c*, based on the data from steps 214*a* and 214*b*.

Once the correlation model is built or updated, the position measurements of the external markers form the dynamic tracking system 402 may be used to compute the corresponding location of the soft tissue target at the scanning rate using the correlation model, step 215. Once the location of the soft tissue target has been computed, the method may include adjusting the radiation beam source position of the treatment delivery system to compensate for the dynamic motion of the soft tissue, step 216. The treatment delivery system 620 may then deliver a dose of radiation to the tracked soft tissue target. In one embodiment, if the delivery of dose is determined not to be completed, step 217, then treatment delivery stage 30 may return to step 214*a* for update of the correlation model. If the delivery of dose has been completed, then method is done, step 218. In another embodiment, the accuracy of the correlation model may be verified or adapted upon obtaining and registering every new set of US images with the latest US image and/or the pre-treatment image (e.g., MR or CT image). In one embodiment, if the correlation model prediction deviates from the US image displacement values and exceeds a specified threshold, then the source of deviation is determined before proceeding. In such an embodiment, previous consecutive US images are compared for consistency (e.g., a US imager may slip on the body surface introducing a false tissue displacement), and marker positions are compared with the correlation model predicted positions to confirm the marker positions.

It should be noted that the displacements of the target as discussed above in relation to FIGS. 1 and 2 may be determined at a different point throughout the registered US image (2D or 3D) or within a region or interest (ROI) or volume of interest (VOI). The displacement values can vary from point to point throughout the registered US image or ROI. Displacement values may be averaged over a specified area (or volume) for an average displacement within a specific region (or volume) of soft tissue or used to determine average tumor displacement within a ROI (or VOI). Spatially varying displacement values may be used to model soft tissue or tumor distortion and localized displacements.

Figure 3:
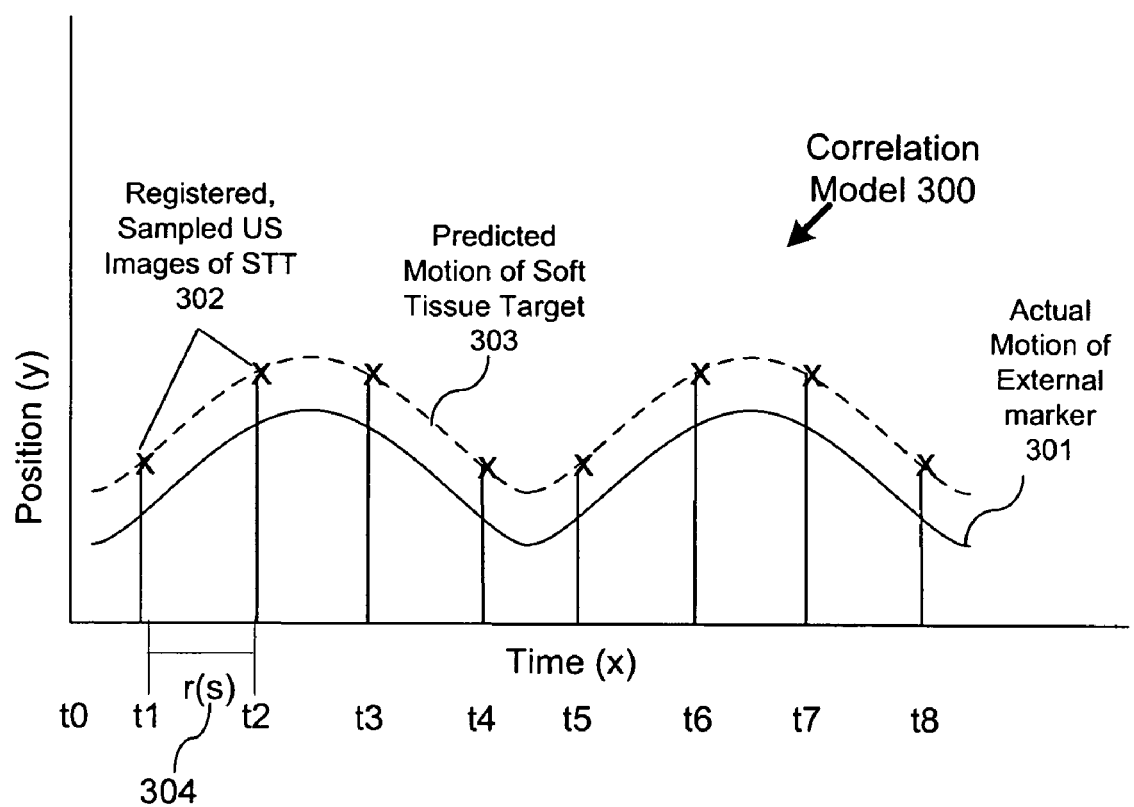
FIG. 3 is a graph illustrating one embodiment of correlating the position of external markers with the registration results from ultrasound images as a function of time for determining the motion of the soft tissue target.

FIG. 3 is a graph illustrating one embodiment of correlating the position of external markers with the registration results from ultrasound images as a function of time for determining the motion of the soft tissue target. Correlation graph 300 includes the position with respect to time of the actual motion of the external markers 301 and the predicted motion of the soft tissue target 303 based on the registration of the sampled US images of the soft tissue target (e.g., registered, sampled US images of the soft tissue target 302). The registered, sampled US images 302 may indicate the position of one or more reference points of the target area of interest in time, sampled at the sampling rate r(s) 304 (e.g., real-time), illustrated by t1-t8. It should be noted that the motion of the external markers 301 and the predicted motion of the soft tissue target 303 have been illustrated as cyclical or sinusoidal so as to illustrate breathing motion of the patient. In another embodiment, the motion may not be cyclical or sinusoidal and may be an irregularly shaped curve. It should also be noted that the accuracy of the predicted motion of the soft tissue target 303 may depend on the sampling rate r(s) 304. The faster the sampling rate r(s) 304 the more registered, sampled US images of the soft tissue target 302 may be used in connection with the actual motion of the external markers 301 in calculating the predicted motion of the soft tissue target 303. The sampling rate r(s) 304, however, may be limited by the computing power of the system, as described above. The actual motion of the external markers 301 has been illustrated a continuous curve. In another embodiment, the detected motion of the external markers 301 may also be discrete values that are sampled at a scanning rate that is higher than the sampling rate of the US images for calculating the predicted motion of the soft tissue target 303.

Figure 2:
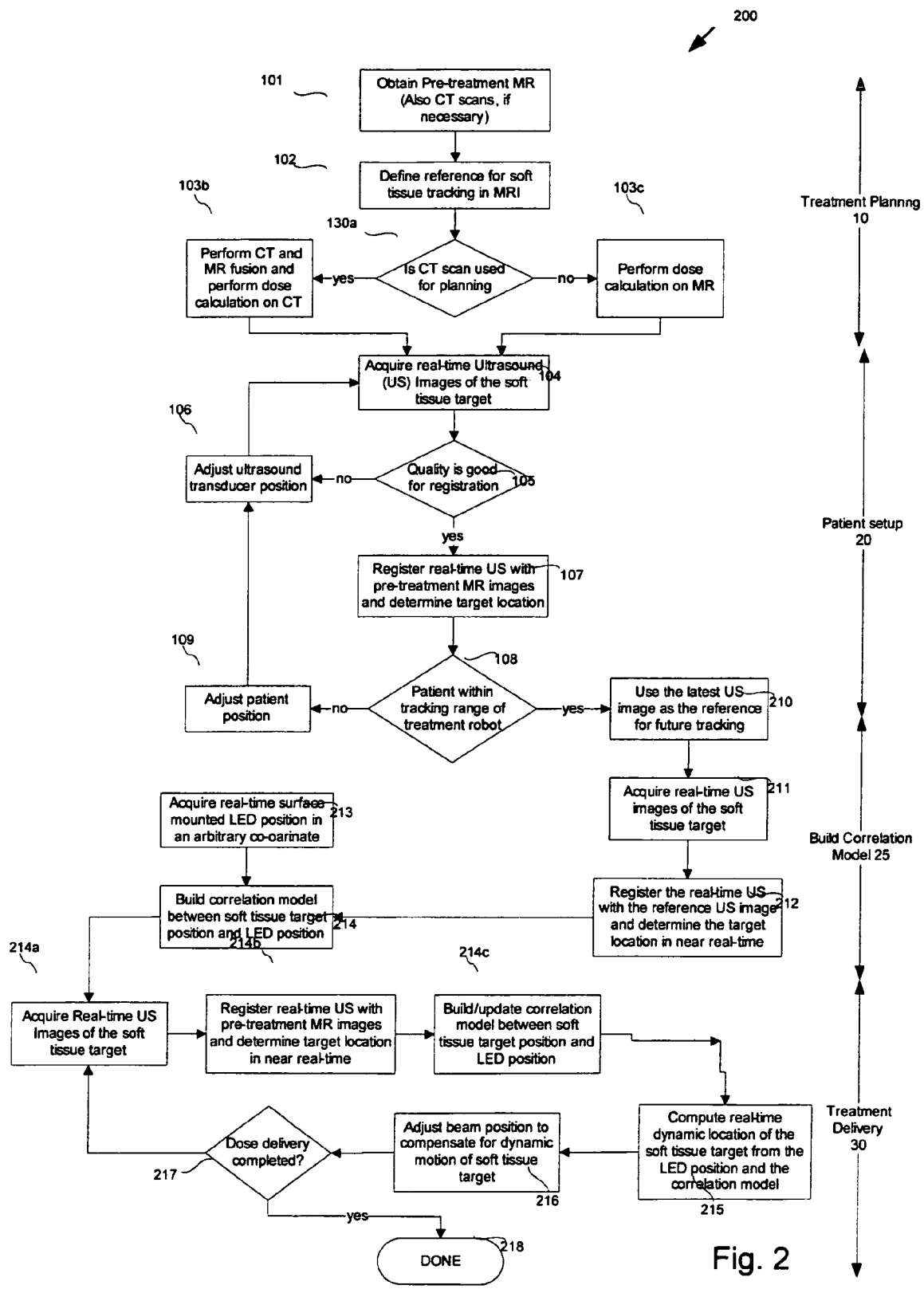
FIG. 2 is a flow chart illustrating another embodiment of workflow for patient radiation treatment that includes real-time tracking of a soft tissue target by combining near real-time US-US registration and real-time tracking of skin surface mounted LED markers.

In one exemplary embodiment of the method described in FIG. 2, at time t1, a sample may be taken of the US images being obtained by the ultrasound imager. The sampled real-time US images may then be registered with either the pre-treatment scan (e.g., MR image) or a latest delivery reference US image. The registration result of the US images may be combined with the real-time motion of the external markers that is being tracked by the dynamic tracking system, which is faster than the sampling rate. Using the registered, sampled US images of the soft tissue target 302 and the actual motion of the external marker 301, the system may calculate the predicted motion of the soft tissue target 303 for dynamically tracking the soft tissue target.

Figure 4:
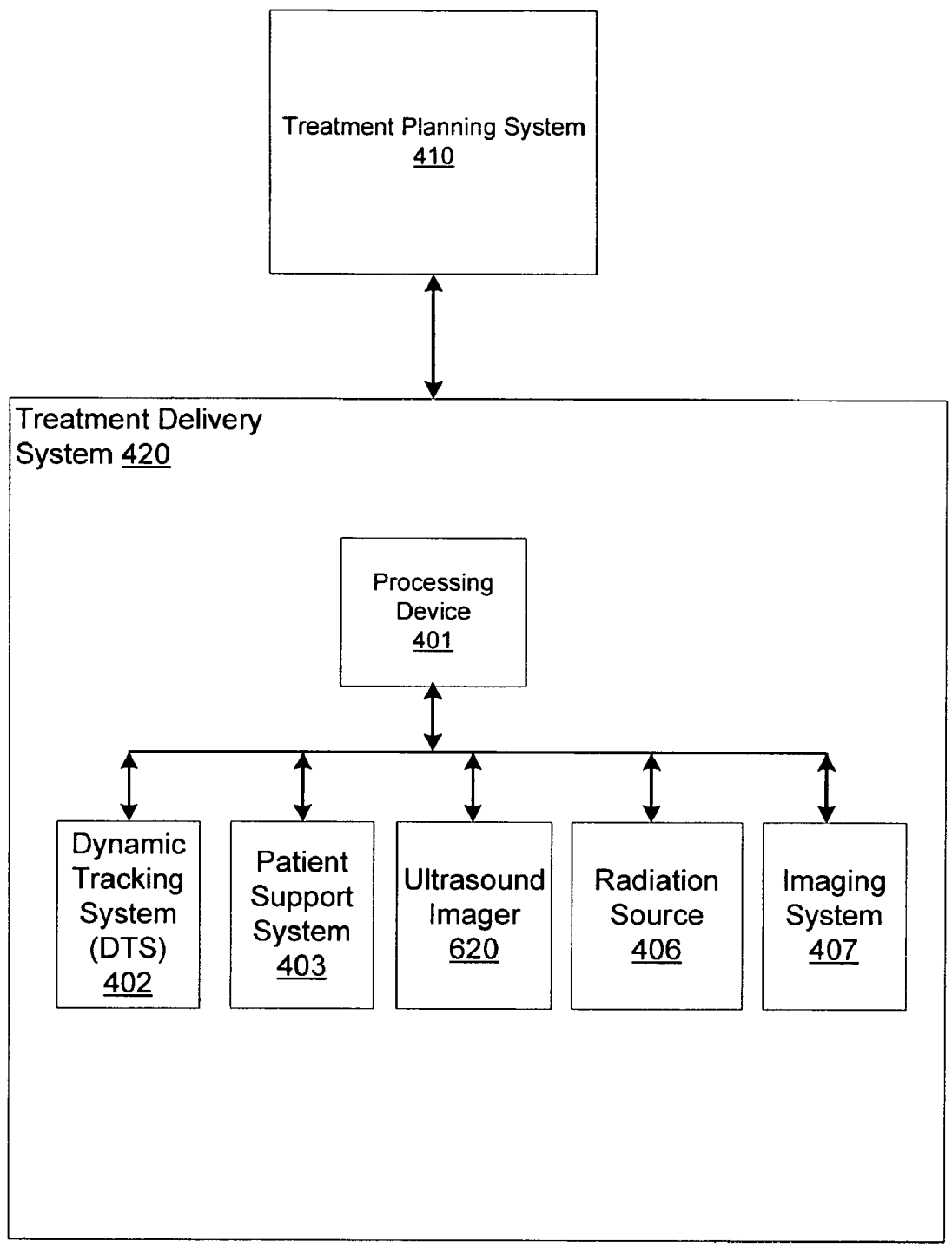
FIG. 4 illustrates a schematic block diagram of one embodiment of a treatment delivery system including a dynamic tracking system for tracking movement of a soft tissue target during radiation treatment.

FIG. 4 illustrates a schematic block diagram of one embodiment of treatment planning system and a treatment delivery system. The treatment planning system 410 may be used to perform the steps discussed above in regards to the treatment planning stage 10, for example, in acquiring the pre-treatment image. The treatment planning system 410 may share its database (e.g., the stored pre-treatment images) with treatment delivery system 420, so that it is not necessary to export from the treatment planning system prior to treatment delivery. The treatment planning system 410 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view isodose distributions on any one of various imaging modalities (e.g., MRI, CT, PET, etc.). Treatment planning systems are known in the art; accordingly, a more detailed discussion is not provided.

The treatment planning system 410 provides the pre-treatment (e.g., MR, CT, etc.) image(s) to the treatment delivery system 420 as a reference for later registration with the ultrasound images acquired by ultrasound imager 620. As previously discussed, the pre-treatment images can be used directly for radiation treatment planning. Alternatively, the pre-treatment images can be fused with other anatomical images (e.g., CT) to perform treatment planning functions. Treatment planning system 410 is used to select a reference point for later measuring the dynamic motions of the soft tissue target. The location of the reference point is provided to the treatment delivery system 420 along with the pre-treatment image.

The treatment delivery system 420 includes a dynamic tracking system (DTS) 402 and a patient support system 403 to position the patient for treatment delivery. The treatment delivery system 420 also include a radiation source 406 to achieve the spatial positions prescribed in the treatment plan and dynamically adjust for the motion of the soft tissue target computed by the dynamic tracking system 402. The dynamic tracking system 402 dynamically tracks the motion of external markers positioned on the patient. Processing device 401 represents one or more general-purpose processors (e.g., a microprocessor), special purpose processor such as a digital signal processor (DSP) or other type of device such as a processing device or field programmable gate array (FPGA), and associate components (e.g., memory), that may located either externally or internally within one or more of the other blocks of system 420. Processing device 401 may be configured to execute the instructions for performing the operations and steps discussed herein. In particular, processing device 401 may be used to perform registration between ultrasound images acquired by ultrasound imager 620 the pre-treatment image, as well as computes the correlation model that relates the motion of the external markers with that of the soft tissue. The treatment delivery system 420 represents only one example of a system, which may have many different configurations and architectures, and which may be employed with the present invention.

In one embodiment, the treatment delivery system 420 may be a frame-less robotic based linear accelerator (LINAC) radiosurgery system, (e.g., the CyberKnife® system developed by Accuray, Inc. of California), as discussed below in relation to FIG. 5. In such a system, the LINAC is mounted on the end of a robotic arm having multiple (e.g., 5 or more) degrees of freedom in order to position the LINAC to irradiate the pathological anatomy with beams delivered from many angles in an operating volume (e.g., sphere) around the patient. Treatment may involve beam paths with a single isocenter, multiple isocenters, or with a non-isocentric approach (i.e., the beams need only intersect with the pathological target volume and do not necessarily converge on a single point, or isocenter, within the target). Treatment can be delivered in either a single session (mono-fraction) or in a small number of sessions (hypo-fractionation) as determined during treatment planning.

Alternatively, another type of treatment delivery system 420 may be used, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. In the IMRT planning, the optimization algorithm selects subsets of the main beam and determines the amount of time for which the subset of beams should be exposed, so that the dose constraints are best met.

In another embodiment, yet other types of treatment delivery system 420 may be used, for example, a stereotactic frame system such as the GammaKnife®, available from Elekta of Sweden. With such a system, the optimization algorithm (also referred to as a sphere packing algorithm) of the treatment plan determines the selection and dose weighting assigned to a group of beams forming isocenters in order to best meet provided dose constraints.

Figure 5:
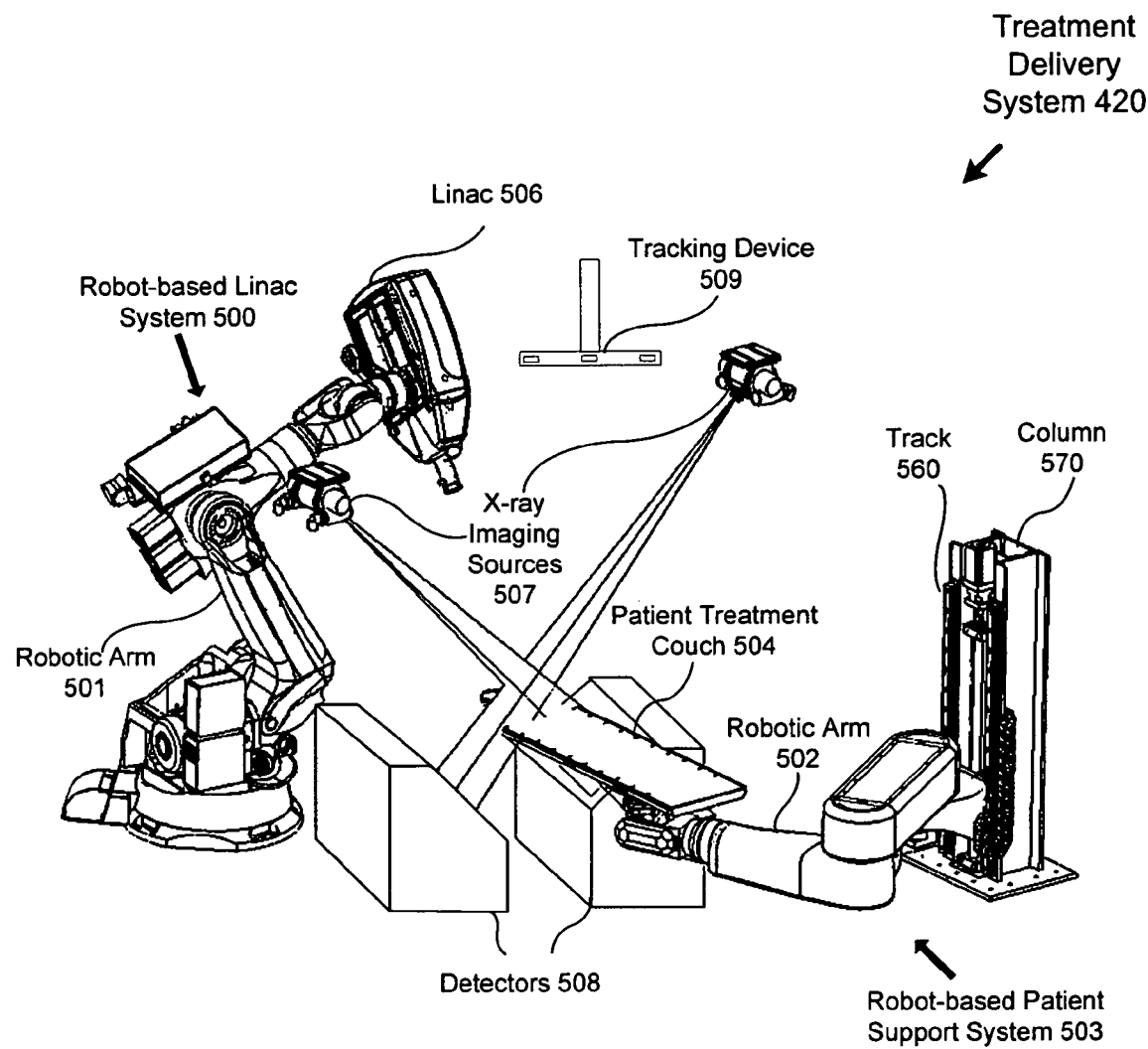
FIG. 5 illustrates one exemplary embodiment of a radiation treatment system using a frameless, image-guided robot-based LINAC system and a robot-based patient support system.

FIG. 5 illustrates one exemplary embodiment of treatment delivery system. In this embodiment, treatment delivery system 420 is a frame-less robotic based LINAC radiosurgery system that includes a robot-based LINAC system 500. The robot-based LINAC system 500 may include a robot, having an articulated robotic arm 501; a LINAC 506 (e.g., radiation source 406) mounted at a distal end of the articulated robotic arm 501, for selectively emitting therapeutic radiation; an x-ray imaging sources 507; detectors 508; a tracking device 509; and a processing device 401 (not shown). In this embodiment, the patient support system 403 is a robot-based patient support system 503. Robot-based patient support system 503 may a robotic arm 502 coupled to a patient treatment couch 504. The robotic arm 502 may have five rotational degrees of freedom and one substantially vertical, linear degree of freedom. Alternatively, the robotic arm 502 may have six rotational degrees of freedom and one substantially vertical, linear degree of freedom or at least four rotational degrees of freedom. The robotic arm 502 may be coupled to a track 560, which is coupled to a column 570. Alternatively the robotic arm may be vertically mounted to a wall, horizontally mounted to a pedestal or to a floor. The column 570 may be mounted to the floor or alternatively it may be mounted to the ceiling. It should also be noted that although FIG. 5 explicitly describes an exemplary embodiment of the patient support system 403 as being robot-based, the patient support system 403 may also be a treatment table mounted to other mechanical mechanisms, such as the Axum® treatment couch developed by Accuray, Inc. of California. Alternatively, the patient support system 403 may be other conventional treatment tables known to those of ordinary skill in the art, such as a treatment table mounted to a stand or pedestal.

In this embodiment, the imaging system 407 of treatment delivery system 420 includes x-ray imaging sources 507 and imaging detectors 508. The x-ray imaging sources 507 may generate image data of the soft tissue target showing the position and orientation of the soft tissue target in a treatment coordinate system or frame. The detector(s) 508 may generate the image information of the patient and send it to the processing device 401. The processing device 401 performs all the imaging calculations to determine the patient's position with respect to the reference treatment position and generate corrections for the various degrees of freedom. The corrections could be automatically applied to the robot-based patient support system 503 to automatically align the patient, and/or sent to the processing device 401 to automatically adjust the patient's position relative to the radiation source 506 of the robot-based LINAC system 500.

In one embodiment, the processing device 401 may be configured to dynamically move, in combination, the patient treatment couch along five rotational degrees of freedom and one substantially vertical, linear degree of freedom using the robotic arm, and the robot-based LINAC system along at least five degrees of freedom using a robotic arm of the robot-based LINAC system to dynamically coordinate orientation and position of the patient treatment couch 504 and a LINAC 506 of the robot-based LINAC system 500. The dynamic coordination of movement between the patient treatment couch and the therapeutic radiation source may position the patient within an operation range (e.g., tracking range) of the LINAC 506 of the robot-based LINAC system 500.

In another embodiment, the processing device 401 may be configured to position the patient treatment couch 504 within an operation range (e.g., tracking range) of the LINAC 506 of the robot-based LINAC system 500. Alternatively, the processing device 401 may be configured to position the LINAC 506 with respect to the patient on the patient treatment couch 504 within the operation range (e.g., tracking range) of the LINAC 506 of the robot-based LINAC system 500.

The processing device 401 may execute treatment planning and treatment delivery software, which may be responsive to pre-treatment scan data (e.g., CT MRI data, PET data and user input, to generate a treatment plan composed of a succession of desired beam paths, each having an associated dose rate and duration at each of a fixed set of treatment positions or nodes. In response to the processing device's instructions, the robotic arm 501 moves and orients the LINAC 506, successively and sequentially through each of the nodes, while the LINAC 506 delivers the required dose as directed by the processing device 401.

Prior to delivering a treatment plan, the patient's position and orientation within the fixed coordinate system or frame of reference established by imaging system 407 must be adjusted by patient treatment couch 504 to match the position and orientation that the patient had within the fixed coordinate system or frame of reference of the pre-treatment (e.g., CT, MRI, PET, etc.) imager that provided the images used for planning the treatment. In one exemplary embodiment, this alignment may be performed to within a position range in which the robotic arm 501 is able to correct for.

As described above, the soft tissue targets, such as a cancerous lesion may not be fixed in relation to a skeletal structure of a patient's body; thus, the position of the soft tissue target may shift during treatment due to motion of the patient, such as breathing motion, organ motion, and other known motions of the body. This means that the soft tissue target may be a moving target. As described above, the methods discussed herein, track the soft tissue target without implanted fiducial markers, allowing the radiation treatment system 400 track internal movements and perform radiosurgery without requiring the patient to hold his/her breathing or gate the LINAC 506 off and on during breathing cycles as required by some conventional systems. In one embodiment, the therapeutic radiation treatment system 400, having DTS 402 for tracking soft tissue targets, may include tracking device 509 and one or more markers externally disposed on the patient. As described above, pre-treatment scans and other diagnostic imaging may be performed during treatment planning. The diagnostic imaging may then be used to model changes in the shape and location of the soft tissue target as the patient breathes, correlating these changes with the movement of the one or more markers externally disposed on the patient, as described above.

In one embodiment, the one or more external markers may be light emitting diodes (LEDs). The LEDs may be visible red or infrared. Alternatively, the external markers may be other markers known to those of ordinary skill in the art, such as laser beacons. In one embodiment, the tracking device 509 of DTS 402 may be mounted to the ceiling of the treatment room. Alternatively, the tracking device 509 may be mounted to other places known to those of ordinary skill in the art, such as the floor or wall of the treatment room.

In one embodiment, during the patient setup stage 10, the patient may be fitted with a conformal elastic vest, including three laser beacons. The laser beacons and corresponding fiber optic cables may be radiolucent, and thus, do not interfere with the imaging or treatment process. The position of these laser beacons may be tracked by tracking device 509. Tracking device 509 may be a linear, three-camera array that scans the treatment room at a scanning rate, such as 32 frames per second, and the resulting images may be processed to determine the spatial coordinates of the laser beacons in the fixed coordinate system. The scanning of the one or more markers may be performed during treatment planning and/or treatment delivery. The motion of the one or more markers, tracked by the tracking device 509, may be combined with the registration results of the US images to predict the motion of the soft tissue targets, as described above with respect to FIGS. 1-3. Alternatively, tracking device 509 may be other known tracking devices known to those of ordinary skill in the art.

Figure 7:
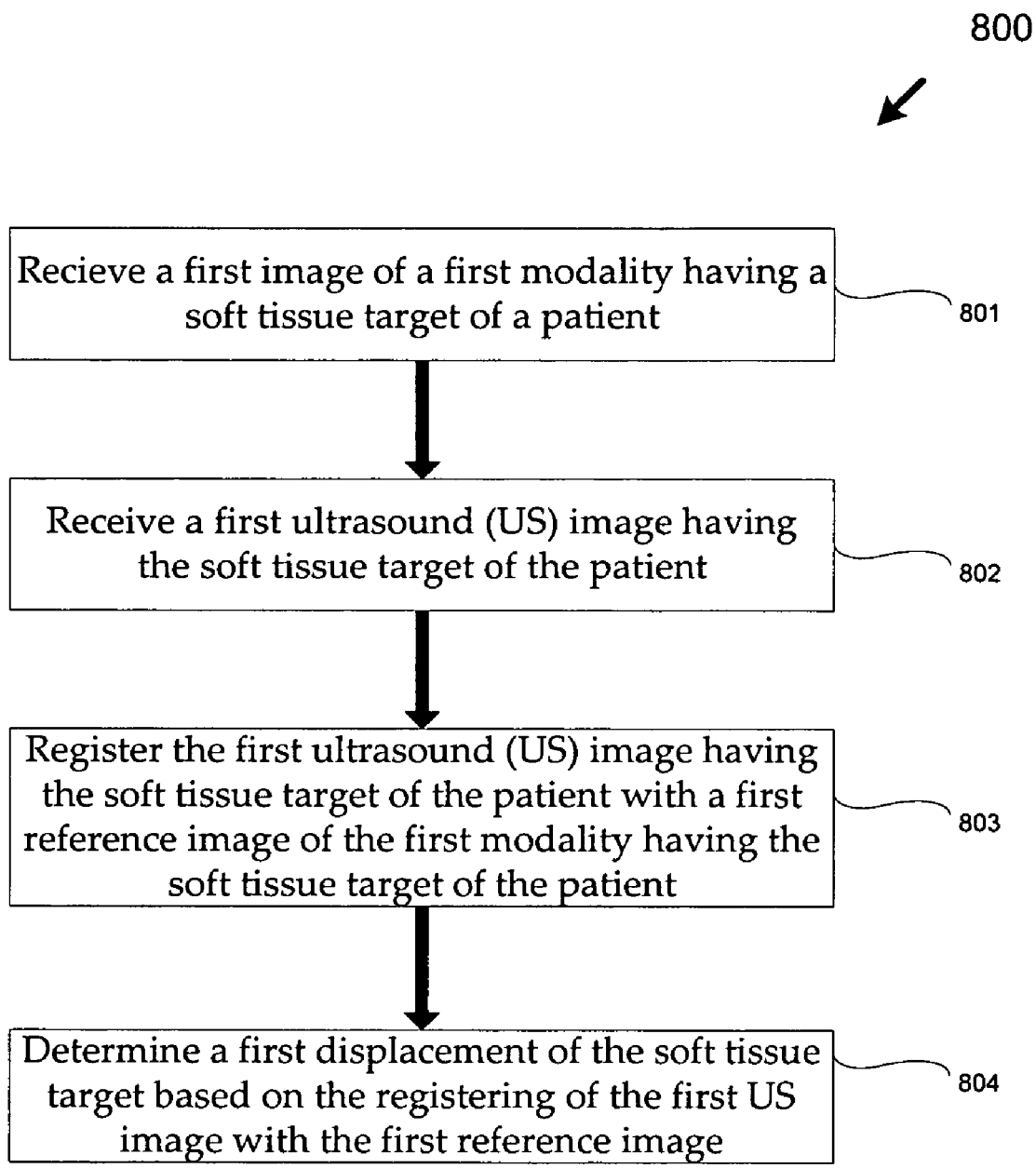
FIG. 7 illustrates one embodiment of a method for determining a displacement of a soft tissue target.

In one embodiment, the DTS 402 may be coupled to (or include) processing device 401, described in more detail in FIG. 7. The processing device 401 may calculate the position and movement of the one or more markers, as well as perform registration and correlation functions described above in FIGS. 1-3. The processing device may also translate or transform the displacements of the soft tissue calculated during registration to positional information to be communicated to the robotic arm 501, which manipulates the corrective movement of the LINAC 506 of the robot-based LINAC system 500 for tracking the internal movement of the soft tissue target.

Figure 6:
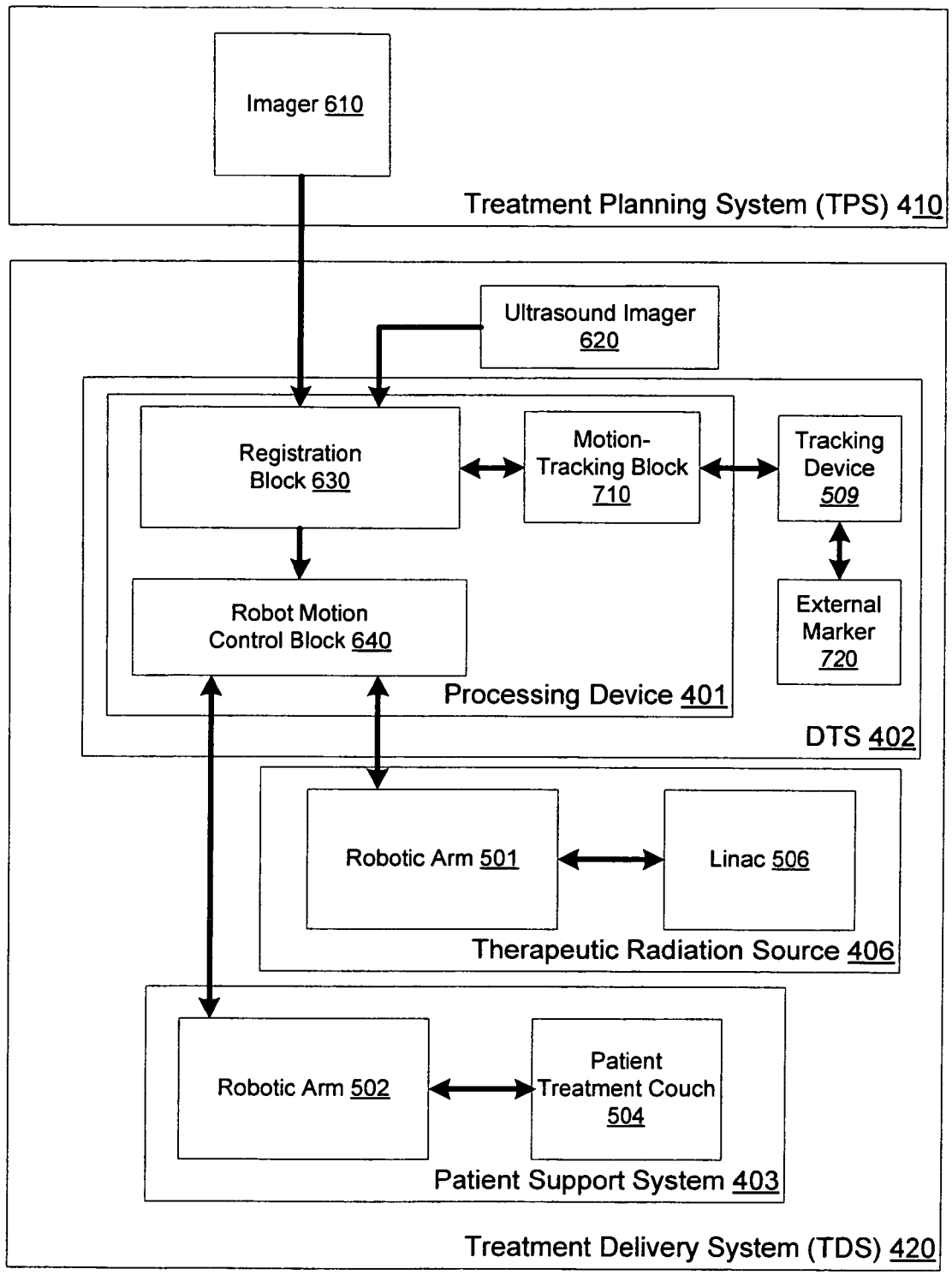
FIG. 6 illustrates a functional block diagram of one embodiment of a treatment delivery system including a dynamic tracking system and an ultrasound imager.

FIG. 6 illustrates a functional block diagram of one embodiment of a treatment delivery system including a dynamic tracking system and an ultrasound imager. The treatment delivery system 420 may include DTS 402 for tracking the soft tissue target, ultrasound imager 620 for obtaining ultrasound images of a soft tissue target, patient support system 403 for positioning the patient for treatment, and a radiation source 406 for delivering a dose of radiation to a treatment target in a patient. DTS 402 may include processing device 401, tracking device 509, and external marker 720. The tracking device 509 may dynamically track the motion of the external marker 720. The external marker 720 may be one or more externally disposed visible red or infrared LEDs. Alternatively, the external marker 720 may be other external markers known to those of ordinary skill in the art.

Processing device 401 may include registration block 630, robot motion control block 640, and motion-tracking block 710. The registration block 630 of treatment planning system 610 may receive the pre-treatment scans of the first modality from imager 610, obtained during treatment planning. Similarly, the registration block 630 may receive ultrasound images from the ultrasound imager 620, obtained during treatment delivery. Ultrasound imager 620 represents one or more ultrasound imagers that may be used as described above. When one or more ultrasound imagers are used, registration may be performed on each image received from the corresponding imagers, and the registration results may be chosen from one of the ultrasound imagers as described above.

The one or more ultrasound imagers 620 may be mounted in such a way that they do not need manual adjustment after an initial patient setup, so that the treatment delivery may be performed without human intervention. In one embodiment, the one or more ultrasound imagers may be mounted using adjustable holder strapped on the patient. Alternatively, the one or more ultrasound imagers may be integrated into a strap or belt that is secured to the patient. The initial adjustment in this form of the sensors may be made manually. Alternatively, the initial adjustments may be made manually, but with assistance from the dynamic tracking system 402. In another embodiment, the processing device 401 of DTS 402 may continually perform registration between the acquired ultrasound images and the pre-treatment image and fed back a quality metric for the registration, as described with respect to FIGS. 1 and 2. The result may be presented as ok/not-ok feedback to the human operator. The human operator may adjust the one or more ultrasound imagers until he gets an 'ok' feedback from the processing device 401 of the DTS 402.

Registration block 630 of processing device 401 may perform registration of the pre-treatment scan and the ultrasound images. Alternatively, registration block 630 may perform registration of two ultrasound images received from the ultrasound imager 620 during treatment delivery. The motion-tracking block 710 receives positional information of the external marker 720 from tracking device 509, and may use the positional information to compute the mathematical model (e.g., correlation model) that relates the motion of the external marker 720 (e.g., one or more LED markers) with that of the registration results of the soft tissue target, determined during registration performed by registration block 630.

As previously described, the processing device 401 may also translate or transform the displacements of the soft tissue, calculated during registration, to positional information to be communicated to the robotic arm 501, which manipulates the corrective movement of the LINAC 506 of the robot-based LINAC system 500 for tracking the internal movement of the soft tissue target (e.g., tumor or lesion). These translations or transformations may be performed in robot motion control block 640.

In one embodiment, robot motion control block 640 of processing device 401 may receive registration results from the registration block 630 and transform this information into corrective motions of the radiation source 406. In one embodiment, the robot motion control block 640 may send corrective motion information to the robotic arm 501 of robot-based LINAC system 500 in order to manipulate the position and orientation of LINAC 506 for tracking the movement of the soft tissue target for delivery of a dose of radiation or for positioning the patient with an operation range of the LINAC 506. The LINAC 506 may be mounted to the robotic arm 501 to achieve the spatial positions prescribed during treatment planning, and dynamically adjust for the motion of the soft tissue target computed by the DTS 402 during treatment delivery. In another embodiment, the robot motion control block 640 may send corrective motion information to the robotic arm 502 of robot-based patient support system 403 in order to manipulate the position and orientation of the patient treatment couch 504 for tracking the movement of the soft tissue for positioning the patient with an operation range of the radiation source 406. The patient treatment couch 504 may be mounted to the robotic arm 502 to achieve the spatial positions prescribed during treatment planning, and dynamically adjust for the motion of the soft tissue target computed by the DTS 402 during treatment delivery. As previously mentioned, the processing device 401 of the DTS 402 may be implemented in processing device 401.

FIG. 7 illustrates embodiments of a method for determining a displacement of a soft tissue target. In one embodiment, the steps of method 800 may represent the steps that are performed in the patient step up stage 20 as described below using the parenthetical examples. In this embodiment, the method 800 includes receiving a first image of a first modality having a soft tissue target of a patient (e.g., the pre-treatment image of step 101 from treatment planning stage 10), step 801, and receiving a first ultrasound (US) image having the soft tissue target of the patient (e.g., the delivery reference US image from an ultrasound imager 620 of step 104, 110 or 210), step 802. In this embodiment, the method 800 also includes registering the first ultrasound image having the soft tissue target of the patient (e.g., the delivery reference US image from an ultrasound imager 620 of step 104, 110 or 210) with a first reference image of the first modality having the soft tissue target of the patient (e.g., the pre-treatment image of step 101 from treatment planning stage 10), step 803. In this embodiment, the method further includes determining a first displacement of the soft tissue target based on the registering of the first US image (e.g., the delivery reference US image from an ultrasound imager 620 of step 104, 110 or 210) with the first reference image, step 804. In this embodiment, the step 804 of determining a displacement may be performed to determine if the patient is within the operational range of a treatment delivery system (e.g., step 108).

Figure 8:
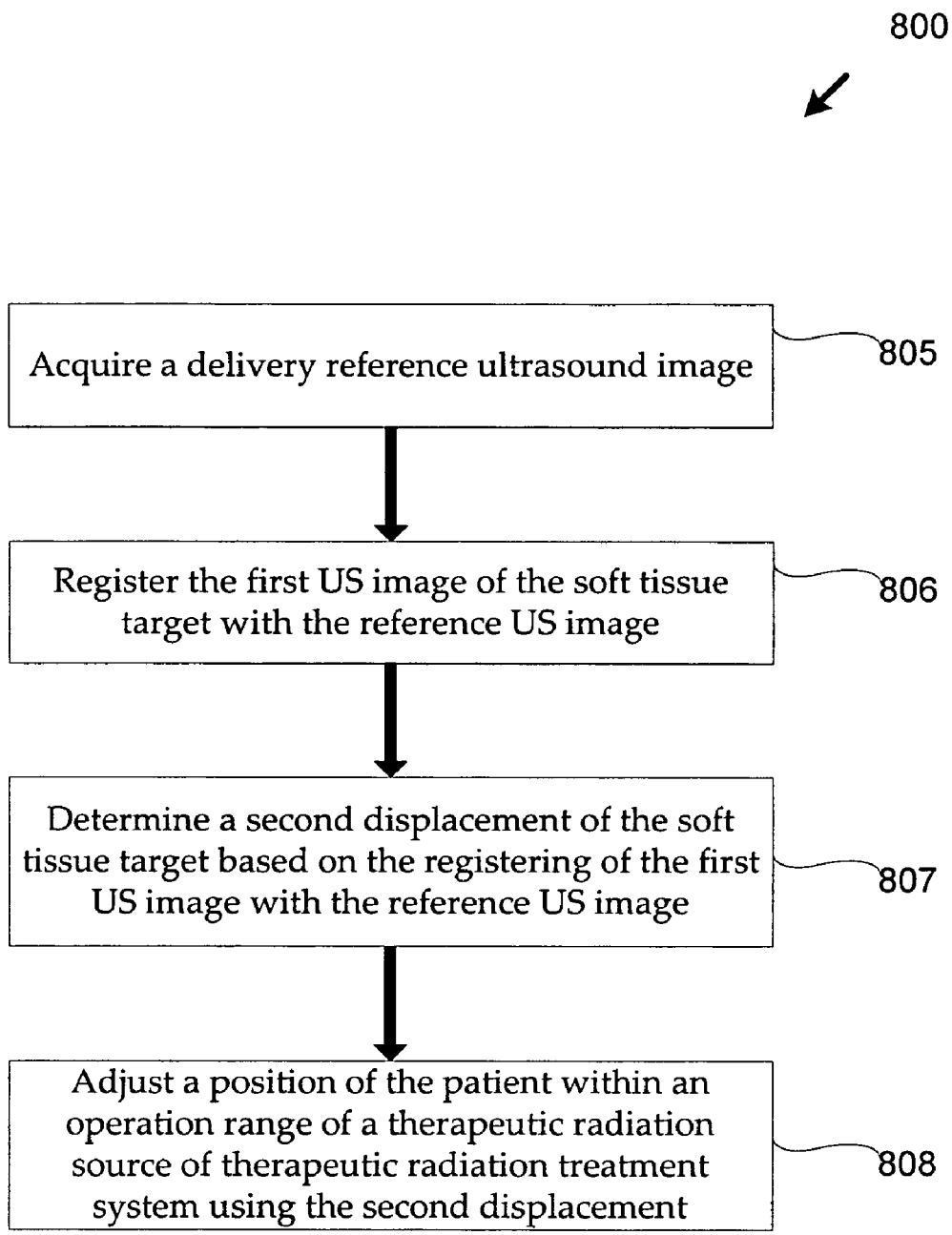
FIG. 8 illustrates another embodiment of a method for determining a displacement of a soft tissue target at a time of treatment delivery.

For this embodiment, where the displacement of step 803 is determined to adjust the position of the patient within the operational range of the treatment delivery system, the method may continue as illustrated in FIG. 8 to dynamically track the external markers and combine the results with subsequent real-time US images during the treatment delivery stage 30. To accomplish such, the method 800 further includes obtaining a delivery reference ultrasound image (e.g., one of the images of step 104, 110 or 210), step 805. Then, in step 806, the first US image of the soft tissue target is registered with the reference US image. In step 807, a second displacement of the soft tissue target based on the registering of the first US image with the reference US image is determined. Step 807 may also include one or more of steps 213-215 to combine the results of the dynamic tracking of external markers with the results of the ultrasound registration to compute a real time dynamic location of the soft tissue target. Then, in step 808, the position of the patient may be adjusted within an operation range of the treatment delivery system 420 using the second displacement.

Referring again to FIG. 7, in another embodiment, the steps of method 800 may represent the steps that are performed in the treatment delivery stage 30 as described below using the parenthetical examples. In this embodiment, the first image of the first modality of step 801 may either be the pre-treatment image obtained in the treatment planning stage 10 or the delivery reference US image from an ultrasound imager 620 of step 104, 110 or 210. The first ultrasound image of step 802 is a subsequent ultrasound image acquired in step 111/211 during the patient delivery stage 30. Accordingly, in this embodiment, the registering of step 803 is a registering of the subsequent (e.g., second) US image of the soft tissue target with the reference US image of the soft tissue target. One or more of steps 213-215 of FIG. 2 to combine the results of the dynamic tracking of external markers with the results of the ultrasound registration of step 803 (not illustrated in FIG. 7) to compute a real time dynamic location of the soft tissue target may also be performed. The displacement of step 803 is determined to adjust the beam position (step 113/216) to compensate for dynamic motion of the soft tissue target during the treatment delivery.

Figure 9:
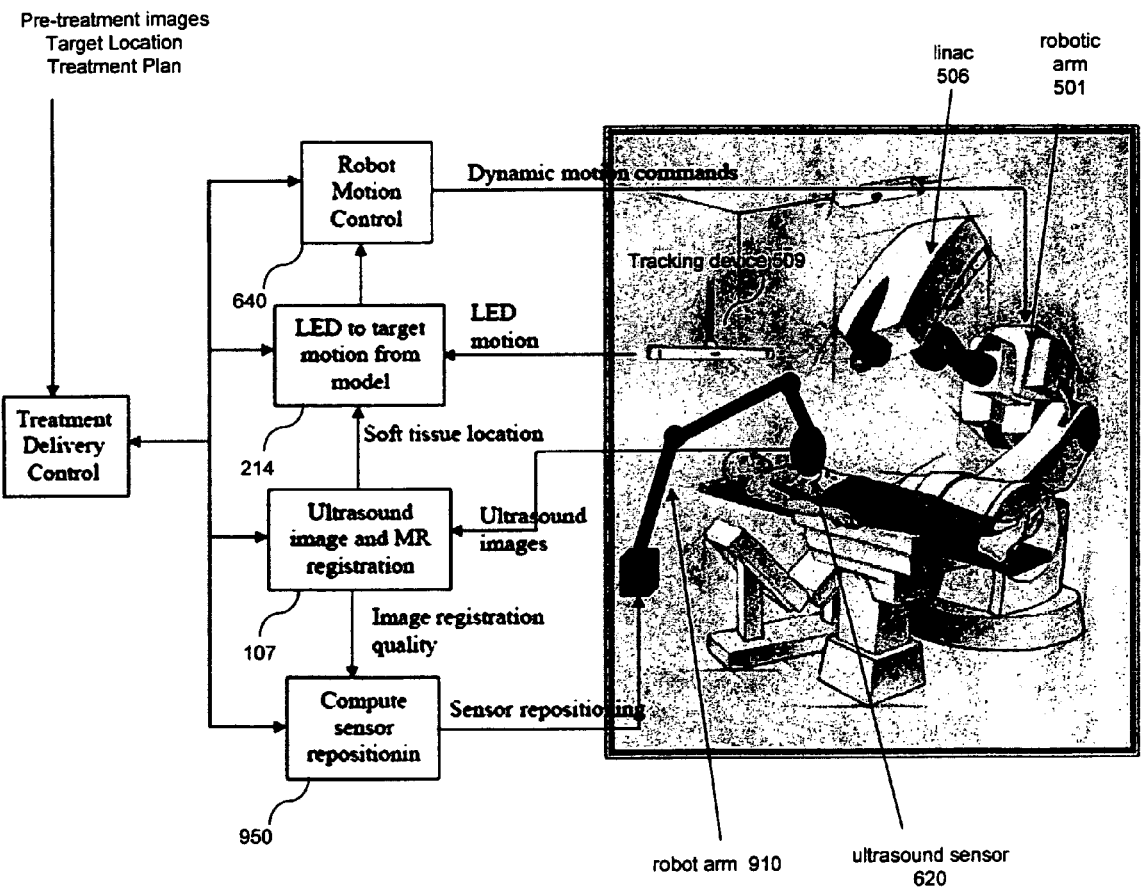
FIG. 9 illustrates one embodiment of dynamic tracking of soft tissue targets using an ultrasound sensor with a robotic arm.

FIG. 9 illustrates one embodiment of dynamic tracking of soft tissue targets using an ultrasound sensor with a robotic arm. In this embodiment, the ultrasound imager, or sensor, may be coupled to a robotic arm 910. The robotic arm 910 may have multiple (e.g., 5 or more) degrees of freedom. The robotic arm 910 may manipulate the ultrasound sensor 620 in small incremental steps. At each step, the acquired ultrasound images may be registered with the pre-treatment image (e.g., MR image), step 107, and a quality metric computed as described above in relation to FIGS. 1 and 2. In block 950, well known optimization techniques may be used to compute the adjustments to be made by the robotic arm 910 (sensor repositioning) such that the quality metric is optimized with respect to the ultrasound senor position. For example, using a steepest gradient search method, the direction of the ultrasound sensor 620 adjustment that improves the quality metric is determined by gradient difference between the metrics from two consecutive measurements, and the adjustment is made in the direction that improves the quality metric. The process may be repeated until an acceptable quality of the image registration is obtained.

Alternatively, the ultrasound sensor 620 may be positioned manually or may be coupled to mechanical positioning mechanisms known in the art. In one embodiment, a combination of manual and robotic positioning of the ultrasound sensor 620 may be employed. Initial course adjustment of the ultrasound sensor 620 is made with assistance from the operator, followed by refinement using the robot and the optimization computations.

Although the robotic arm 910 and ultrasound sensor 620 of FIG. 9 are illustrated with a robotic based linear accelerator (LINAC) radiosurgery system, it should be noted that robotic positioning of ultrasound sensor 620 may also be utilized with another type of treatment delivery system 420 as discussed above.

In the foregoing specification, embodiments of the invention have been described with reference to specific exemplary embodiments thereof. It will, however, be evident that various modifications and changes may be made thereto without departing from the broader spirit and scope of the present embodiments as set forth in the claims. The specification and drawings are, accordingly, to be regarded in an illustrative rather than a restrictive sense.

What is claimed is:

1. A method for dynamic tracking of soft tissue targets comprising:
    registering a first ultrasound (US) image having a soft tissue target of a patient with a first reference image of a first modality having the soft tissue target of the patient;
    determining a first displacement of the soft tissue target based on the registering of the first US image with the first reference image;
    registering a second US image of the soft tissue target with the first US image of the soft tissue target, wherein the second US image is obtained subsequent to the first US image;
    determining a second displacement of the soft tissue target based on the registration of the second US image with the first US image;
    adjusting a position of a radiation source of radiation treatment delivery system using the second displacement;
    storing the second US image to establish a treatment delivery reference position of the soft tissue target for registration with one or more subsequent US images; and
    registering the one or more subsequent US images with the treatment delivery reference position to determine a third displacement of the soft tissue target with respect to the treatment delivery reference position of the soft tissue target, wherein the one or more subsequent US images are obtained at a first rate, and wherein determining the third displacement further comprises:
        tracking a second motion of one or more markers externally disposed on the patient by sensing the one or more markers at a second rate with respect to a fixed coordinate system, wherein the second rate is higher than the first rate; and
        calculating a predicted position of the soft tissue target as a function of a time using a correlation model based on tracking the second motion of the one or more markers, the correlation model correlates the second motion of the one or more markers to the predicted position of the soft tissue target; and readjusting the position of the radiation source using the third displacement.

2. The method of claim 1, wherein the first rate is less than approximately 60 Hz and wherein the second rate is greater than approximately 1 Hz.

3. The method of claim 1, wherein predicting the position of the soft tissue target comprises:

determining a second position of the one or more markers as a function of time based on tracking the second motion in the fixed coordinate system;

registering one or more subsequent US images; and combining the registration results with the position of the one or more markers to compute a location of the soft tissue target in real time.

4. The method of claim 1, further comprising determining whether the predicted position of the soft tissue target in the correlation model deviates from the third displacement in excess of a specified threshold and, if so, comparing previous consecutive US images for consistency; and comparing positions of the one or more markers with the correlation model predicted positions to confirm the positions of the one or more markers.

5. The method of claim 3, wherein the position of one or more external markers is interpolating to a point in time corresponding with an US image or for interpolating between a plurality of US images to create a new image corresponding to the one or more external marker positions.

* * * * *